United States Patent [19]
Hunt et al.

[11] Patent Number: 5,703,252
[45] Date of Patent: Dec. 30, 1997

[54] RECOVERY OF TOCOPHEROLS

[75] Inventors: Tracy K. Hunt, Kankakee, Ill.; Joerg Schwarzer, Hilden, Germany

[73] Assignee: Henkel Corporation, Plymouth Meeting, Pa.

[21] Appl. No.: 753,460

[22] Filed: Nov. 25, 1996

Related U.S. Application Data

[60] Provisional application No. 60/008,762 Dec. 13, 1995.

[51] Int. Cl.$^6$ .................................................. C07D 311/72
[52] U.S. Cl. .................................................. 549/413
[58] Field of Search .................................................. 549/413

[56] References Cited

U.S. PATENT DOCUMENTS

| | | |
|---|---|---|
| 2,432,181 | 12/1947 | Trent . |
| 2,729,655 | 1/1956 | Miller et al. . |
| 3,153,055 | 10/1964 | Brown et al. . |
| 3,335,154 | 8/1967 | Smith . |
| 3,840,570 | 10/1974 | Julian . |
| 4,148,810 | 4/1979 | Struve . |
| 4,374,776 | 2/1983 | Struve et al. . |
| 4,451,564 | 5/1984 | Struve et al. . |
| 5,190,618 | 3/1993 | Top et al. . |
| 5,424,457 | 6/1995 | Sumner et al. . |

FOREIGN PATENT DOCUMENTS

| | | |
|---|---|---|
| 171009 | 12/1986 | European Pat. Off. . |
| 3126110 | 4/1982 | Germany . |
| WO9504731 | 2/1995 | WIPO . |

OTHER PUBLICATIONS

*Fat Sci. Technol.*, vol 91, 1989, pp. 39–41.
*Ulmanns Enzyklopaedie der Technischen Chemie*, 4th Edition, vol. 23, 1984, p. 645.

*Bailey's Industrial Oil and Fat Products*, vol. 3, pp. 127–165 (John Wiley & Sons, Inc., NY, NY 1985).

*Encyclopedia of Chemical Technology*, vol. 9, pp. 306–308 (Kirk–Othmer, eds., John Wiley & Sons, Inc., NY, NY 1980.

E. Hafslund, "Distillation", *Encyclopedia of Chemical Technology*, vol. 7, pp. 849–891 (Kirk–Othmer, eds, John Wiley & Sons, NY, 3d ed. 1979.

F. Standiford, "Evaporation",*Encyclopedia of Chemical Technology*, vol. 9, pp. 472–493 (Kirk–Othmer, eds, John Wiley & Sons, NY 3d ed. 1980.

*Encyclopedia of Chemical Technology*, vol. 7, pp. 243–285 (Kirk–Othmer, eds. John Wiley & Sons, NY, 3d ed. 1979.

*Handbook of Chemistry and Physics*, pp. E–56 to E–58 (CRC Press, Inc., Cleveland, Ohio, 55th ed. 1974).

*Primary Examiner*—Nicky Chan
*Attorney, Agent, or Firm*—Wayne C. Jaeschke; J. Daniel Wood; John E. Drach

[57] ABSTRACT

Starting from a mixture containing tocopherol, fats and/or fat derivatives, more particularly fatty acids, and optionally sterol and/or sterol derivatives, the free fatty acids present in the mixture are esterified with an alcohol and fatty glycerides are transesterified with an alcohol in the presence of a zinc oxide and/or zinc hydroxide catalyst. After the esterifications, the excess lower alcohol is distilled off from the reaction mixture. The transesterification catalyst and the glycerol present, if any, are removed and the fatty acid alkyl ester is distilled off from the mixture. Distillation of fatty acid alkyl esters can be accomplished with a packed column in sequence with a wiped film evaporator. The simultaneous recovery of tocopherol and sterol is possible. Tocopherols and sterols can be separated by the crystallization of sterols from a blend of organic solvents.

22 Claims, No Drawings

5,703,252

RECOVERY OF TOCOPHEROLS

CROSS-REFERENCE TO RELATED APPLICATIONS

This application claims priority from U.S. provisional application Ser. No. 60/008,762 filed Dec. 13, 1995, the disclosure of which is incorporated herein by reference.

FIELD OF THE INVENTION

This invention relates to a process for recovering tocopherol and, optionally, sterol from a mixture containing tocopherol, fats and/or fat derivatives, more particularly fatty acids, and optionally sterol and/or sterol derivatives.

BACKGROUND ART

Tocopherol compounds occur in many vegetable and animal oils and are also referred to as vitamin E. The vitamin E relates to the physiological effect of these food ingredients.

There are 8 naturally occurring substances with vitamin E activity. They are derivatives of 6-chromanol and belong to two groups of compounds. The first group is derived from tocol and carries a saturated isoprenoidal side chain containing 16 carbon atoms. This group includes alpha-, beta-, gamma-, and delta-tocopherol. The compounds differ in their degree of methylation at the benzene ring of the tocol. Alpha-tocopherol is the substance with the strongest biological vitamin E effect and the greatest technical and economical importance. It is the dominant tocopherol in human and animal tissue.

The second group of substances with vitamin E activity are the derivatives of tocotrienol. They differ from the other tocopherol homologues in the unsaturated isoprenoidal side chain containing 16 carbon atoms. The naturally occurring tocotrienols also show vitamin E activity and are normally isolated from their natural sources together with the saturated tocopherol homologs in the recovery of vitamin E. In the context of the present invention, the name "tocopherol" is also intended to encompass these tocopherol homologs, i.e. tocopherol are found in vegetable oils, such as wheatgerm oil, corn oil, soybean oil and palm kernel oil. However, tocopherol is also found in other vegetable oils, for example in safflower oil, peanut oil, cottonseed oil, sunflower oil, rapeseed oil, palm oil and other vegetable oils.

The natural plant oils contain only small quantities of tocopherol. Concentration is undesirable for commercial applications. In addition, impurities are supposed to be removed to enhance the antioxidizing effect and vitamin E activity. Accordingly, the most important natural sources of tocopherol are not the vegetable oils themselves, but rather the steam distillates, also known as steamer distillates, obtained in the deodorization of vegetable and animal oils. Although the tocopherols are obtained in concentrated form, they are mixed with sterol and sterol esters, free fatty acids and triglycerides. The distillate from the deodorization of soybean oil is particularly interesting. The particular suitability of soybean oil as a source of tocopherols is mentioned, for example, in *Fat Sci. Technol.*, Vol. 91, 1989, pages 39 and 41 in a comparison of the deodorization distillates of soybean oil and rapeseed oil. The soybean oil steamer distillate contains approximately 10% (maximum) by weight mixed tocopherols and the same amount of sterols which are predominantly present in their ester form.

There are various known processes for the concentration of tocopherol, namely esterification, saponification and fractional extraction. Thus, according to DE 31 26 110 A1, tocopherol concentrates are obtained from secondary products of the deodorization of oils and fats by esterification of the free fatty acids present therein by addition of an alcohol or by removal of the free fatty acids from the distillates by distillation, after which these products are subjected to hydrogenation and subsequently to solvent fractionation to extract the tocopherols. Another process for concentrating tocopherol is known from the same document. In this process, the deodorization distillates are subjected to transesterification with methanol and the fatty acid methyl esters are distilled off. The residue is concentrated by molecular distillation.

In another process known from EP 171 009 A2, the tocopherol-containing material is contacted with a sufficient quantity of a polar organic solvent which dissolves the tocopherols, but not the impurities. The polar phase enriched with tocopherol is separated off and the tocopherol is recovered therefrom.

It is also known that the tocopherols can be separated by adsorption onto basic anion exchangers. This variant is possible if the mixture contains little, if any, fatty acid. The sterols, glycerides and other neutral or basic substances are not adsorbed (*Umanns Enzyklopädie der Technischen Chemie*, 4th Edition, Vol. 23, 1984, page 645).

It is also known that sterols can be separated from tocopherols by fractional crystallization after concentration. In this process, tocopherol passes into solution and sterol crystallizes out. Tocopherol and sterol can also be separated by distillation, except that in this case the sterol is at least partly destroyed. Accordingly, two useful products are obtained after the separation of tocopherol and sterol.

In a variant described in DE 31 26 110 A1, tocopherol is subjected to molecular distillation or to steam distillation after esterification of the free acids with polyhydric alcohols in order to obtain a distillate having a high tocopherol content. However, the process step of molecular distillation is uneconomical on an industrial scale while steam distillation involves exposure to relatively high temperatures which at least partly destroys the sterols. In the latter case, therefore, only the thermally more stable tocopherol can be obtained in high yields.

Numerous methods have been proposed for the recovery of tocopherols and sterols from deodorizer distillates and related mixtures. For example, U.S. Pat. No. 2,432,181 discloses that tocopherols can be recovered from vegetable oils and fats by reacting the fatty acid glycerides with an aliphatic monohydric alcohol in the presence of an alkaline alcoholysis catalyst, followed by flash distillation of residual alcohol, glycerol and fatty acid esters.

U.S. Pat. No. 2,729,655 discloses that sterols can be recovered from distillate by saponification and acidulation to convert glycerides and sterol esters to free fatty acids and free alcohols (glycerol, sterols respectively). The free fatty acids are esterified with a monohydric lower alcohol. The sterols are crystallized by the addition of a hydrocarbon/water solvent to the mixture.

U.S. Pat. No. 3,153,055 discloses a process for the isolation of sterols and tocopherols from deodorizer distillate by esterification of higher fatty acids into lower monohydric alcohol esters under strongly acidic conditions. The sterols and tocopherols are fractionally extracted from the esterification product with a combination of polar and nonpolar solvents.

U.S. Pat. No. 3,335,154 discloses that the distillate is saponified and acidulated to convert glycerides and sterol esters to free fatty acids and free alcohols (glycerol, sterols respectively). The free fatty acids are esterified with a monohydric lower alcohol and mineral acid catalyst. The sterols are precipitated by the addition of water to the mixture, and the tocopherols are concentrated by removal of the fatty esters by molecular distillation.

U.S. Pat. No. 3,840,570 discloses that sterols can be concentrated from a plant-derived source by phase separation caused by the addition of a water-alcohol solvent. Sterol esters are saponified with an alkali metal base and free sterols are crystallized from an aprotic solvent.

U.S. Pat. No. 4,148,810 discloses that sterols can be isolated by transesterification of distillate with methanol, catalyzed by alkali metal alcoholates or alkali metal hydroxides. The sterols are isolated from the transesterification mixture by adduct formation with calcium chloride in an aprotic solvent.

U.S. Pat. Nos. 4,374,776 and 4,451,564 disclose a method for the concentration of sterols by base-catalyzed transesterification of distillate residues with a lower monohydric alcohol, followed by molecular distillation. The base catalyst is an alkali metal alcoholate or alkali metal hydroxide. The use of alkaline transesterification catalysts in the methods discussed above suffer a major disadvantage in that they require that the mixture be free of all acidic components that would neutralize the alkaline catalyst. This is most unsatisfactory in the case of tocopherols in that they are phenolic compounds and can react with methoxide ion. Other drawbacks of the above processes are that they require multiple reactor systems and processing steps, product purification, relatively low yields, and low through-put.

U.S. Pat. No. 5,424,457 discloses a process in which deodorizer distillate is subjected to an esterification/transesterification step utilizing a lower alcohol and an alkyltin catalyst, crystallization to remove sterols, followed by distillation to remove lower alcohol and the fatty acid lower alcohol esters, and finally a molecular distillation to concentrate the tocopherols. Alternatively, the lower alcohols and/or fatty acid lower alcohol esters may be removed prior to crystallization. There is also disclosed a process for the alkyltin catalyzed esterification/transesterification of free fatty acids and fatty acid esters in the presence of tocopherols in which approximately 55 to 90% of the sterol esters are converted.

SUMMARY OF THE INVENTION

This invention relates to a process useful in the recovery of tocopherols from a tocopherol mixture comprised of fatty acids and tocopherols, said process comprising esterifying free fatty acids present in said tocopherol mixture and transesterifying fatty acid glyceride esters present in said tocopherol mixture by mixing said tocopherol mixture with a lower alcohol (preferably a member selected from the group consisting of primary and secondary mono-alkanols having less than five carbon atoms) in the presence of a zinc catalyst selected from the group consisting of zinc oxide and zinc hydroxide, and mixtures thereof, to form a reaction mixture in a reaction vessel, the temperature of said reaction mixture being above the atmospheric boiling point of said alcohol and the pressure within said reaction vessel being sufficient to maintain at least a major proportion of said alcohol in a liquid phase. The process typically further comprises distilling excess lower alcohol from the product and washing the product (preferably first with an aqueous mineral acid followed by washing with pure water) to remove said zinc catalyst and glycerol produced by said transesterification.

In preferred embodiments, the product of the above-described process is dried and mixed with a lower alcohol (preferably a member selected from the group consisting of primary and secondary mono-alkanols having less than five carbon atoms) in the presence of an alkoxide catalyst selected from the group consisting of alkali metal alkoxides of said alcohol, to form a reaction mixture in a reaction vessel, the temperature of said reaction mixture being above the atmospheric boiling point of said alcohol and the pressure within said reaction vessel being sufficient to maintain at least a major proportion of said alcohol in a liquid phase. In these preferred embodiments, the process typically further comprises distilling excess lower alcohol from the product of said transesterification (and preferably recycling at least a portion of said distilled methanol to said esterifying and transesterifying step) and washing the product of said transesterification (preferably first with an aqueous mineral acid followed by washing with pure water) to remove glycerol produced by said transesterification.

DETAILED DESCRIPTION OF THE INVENTION

The starting material for the process of the invention is a mixture which contains fatty compounds and sterol compounds in addition to tocopherols. A major advantage of the process according to the invention is that it can be applied to various mixtures containing tocopherol and, optionally, sterol. In particular, however, it is of advantage to start out from soybean oil steamer distillate which is obtained by steam distillation of crude soybean oil as the first stage of the deodorization process. Oil deodorization is discussed in *Bailey's Industrial Oil and Fat Products*, vol. 3, pp. 127–165, (John Wiley & Sons, Inc. N.Y., N.Y., 1985), the disclosure of which is incorporated herein by reference. The distillates contain about 8 to about 20% sterol (e.g. about 12%), about 3 to about 5% tocopherol (e.g. about 8%), about 20 to about 35% free fatty acids and, as its principal constituent, triglycerides (Ullmans, loc. cit.). However, steamer distillates of other oils, for example rapeseed oil distillates, can also be processed by the process according to the invention.

The process according to the invention is by no means limited in its application to steamer distillates of vegetable oils and fats. It may also be applied with advantage to tall oil. Tall oil is, economically, one of the most important secondary products of the cellulose sulfate process used in paper-making. It is obtained by acidification of the sodium salt mixture or resinic and fatty acids formed in this process. Tall oil is a natural mixture of resinic acids of the abietic acid type, saturated and unsaturated fatty acids and fatty acid esters and an unsaponified fraction. In addition to higher alcohols and hydrocarbons, the unsaponifiable fraction also contain sterols.

Other mixtures containing tocopherol may also be worked by the process according to the invention, for example the residue obtained in the production of rapeseed oil methyl ester which also contains sterols and sterol esters.

In the process, the free fatty acids and fatty glyceride esters present in the starting mixture are reacted with a lower alcohol to form fatty acid alkyl esters, more particularly fatty acid methyl esters. The partial glycerides and triglycerides react to form glycerol and fatty acid alkyl esters. In the certain embodiments, sterol fatty acid ester is reacted to produce sterols and fatty acid alkyl esters in a second separate step. The tocopherol present in the mixture does not react in either step.

The fatty acids in the tocopherol mixture are esterified and the fatty glycerides are transesterified, preferably with a lower alcohol, preferably a $C_1$ to $C_4$ mono-hydric alkanol, e.g. methanol, ethanol, n-propanol, isopropanol, n-butanol, or tert-butanol. The alcohol and zinc catalyst are typically added to a reaction vessel containing the tocopherol mixture. Alcohol is present in the reaction mixture during the esterification, preferably in stoichiometric excess of fatty acids and esters in the product. Typically, an amount of alcohol of about 20% to about 80%, more typically about 50% to about 60%, with respect to the mass of original tocopherol containing starting material is employed to facilitate conversion of the fatty acids and fatty glyceride esters to alkyl fatty acid esters.

The reaction is catalyzed by an effective amount of zinc oxide and/or zinc hydroxide. The amount of catalyst will typically range from about 0.005% to about 5% by weight of the tocopherol mixture, more typically from about 0.01% to about 1%, and even more typically from about 0.05% to about 0.2%.

The esterification and transesterification are preferably conducted at a temperature between about 150° C. and about 240° C. and in reaction times of 10 minutes or more, e.g. about 1 to about 3 hours. The vessel will be pressurized to maintain a liquid reaction phase at these temperatures. The reaction is conducted until the desired degree of esterification and transesterification is obtained, preferably until a major proportion (e.g. more than about 50% by weight, typically at least about 90%) of the fatty acids and fatty glyceride esters are esterified to produce alkyl fatty esters. The catalyst should then be neutralized with an essentially equal stoichiometric amount of acid, preferably aqueous sulfuric acid (preferably at about 1–10% by weight of acid). The excess alcohol (and any now free higher alcohol) should then be distilled from the mixture (e.g. in a series of simple distillation of lower alcohol followed by simple distillation of higher alcohol) prior to optional treatment with a chelating chemical (such as ascorbic acid (vitamin C), phosphoric acid, maleic acid, citric acid or tartaric acid), followed by water washing (to remove glycerol and salts), and optional nitrogen sparging and drying.

For the next process step, removal of the excess lower alcohol by distillation, it is of particular advantage if a short-chain alcohol, more particularly methanol, has been used in the preceding steps. In this way, exposure to high temperatures can be minimized. Before removal of the alkyl fatty acid ester by distillation, it is advisable not only to separate the glycerol formed in the transesterification step from triglycerides present, if any, but also to remove the esterification/transesterification catalyst. The catalyst is largely present in the form of zinc salts which could be problematical during distillation and could lead, for example, to an increase in the boiling point. A highly concentrated tocopherol/sterol mixture is obtained after removal of the fatty acid alkyl ester. The tocopherol and sterol in this mixture can be separated from one another by methods known per se, for example by crystallization.

If essentially complete conversion of sterol esters in the tocopherol mixture to free sterols is desired, the product is then transesterified in the presence of an alkoxide catalyst, e.g. a lower alkoxide (preferably in a solution of the same lower alkanol, e.g. sodium methoxide in methanol.) Transesterification reactions are discussed in *Encyclopedia of Chemical Technology*, vol. 9, pp. 306–308 (Kirk-Othmer, eds., John Wiley & Sons, Inc., N.Y., N.Y., 1980), the disclosure of which is incorporated by reference.

The sterol esters in the esterification/transesterification reaction product can be transesterified, preferably with a lower alcohol, preferably a $C_1$ to $C_4$ mono-hydric alkanol, e.g. methanol, ethanol, n-propanol, isopropanol, n-butanol, or tert-butanol. The alcohol and an alkoxide catalyst, such as sodium methoxide, are typically added to a reaction vessel. Alcohol is present in the reaction mixture during the esterification, preferably in stoichiometric excess of fatty sterol esters in the product. Typically, an amount of alcohol of about 20% to about 80%, more typically about 50% to about 60%, with respect to the mass of original tocopherol containing starting material is employed to facilitate conversion of the fatty sterol esters to alkyl fatty acid esters and free sterols. There should be essentially no water present in the reaction medium during transesterification (e.g. less than about 0. 1% by weight) to avoid the formation of soaps and/or destroy the catalyst. Thus, the esterification/transesterification product should be dried, e.g. by air stripping.

The reaction is catalyzed by an effective amount of an alkoxide catalyst. The amount of catalyst will typically range from about 0.01% to about 10% by weight of the tocopherol mixture, more typically from about 0.05% to about 2%, and even more typically from about 0.1% to about 0.5%.

The transesterification of sterol esters is preferably conducted at a temperature between about 150° C. and about 240° C. and in reaction times of 10 minutes or more, e.g. about 1 to about 3 hours. The vessel will be pressurized to maintain a liquid reaction phase at these temperatures. The reaction is conducted until the desired degree of esterification and transesterification is obtained, preferably until a major proportion (e.g. more than about 50% by weight, typically at least about 90%) of the fatty acids and fatty glyceride esters are esterified to produce alkyl fatty esters. The catalyst should then be neutralized with an essentially equal stoichiometric amount of acid, preferably aqueous sulfuric acid (preferably at about 1–10% by weight of acid). The excess alcohol (and any now free higher alcohol) should then be distilled from the mixture (e.g. in a series of simple distillation of lower alcohol followed by simple distillation of higher alcohol) prior to optional treatment with a chelating chemical (such as ascorbic acid (vitamin C), phosphoric acid, maleic acid, citric acid or tartaric acid), followed by water washing (to remove glycerol and salts), and optional nitrogen sparging and drying.

The esterification steps performed above yield a mixture comprised of tocopherols, sterols and alkyl fatty acid esters. The alkyl fatty acid esters can be separated from the mixture as a distillate. The distillation should be accomplished in a manner such that unacceptable degradation of the tocopherols and/or sterols is avoided. Distillation is discussed in E. Hafslund, "Distillation", *Encyclopedia of Chemical Technology*, vol. 7, pp. 849–891 (Kirk-Othmer, eds. John Wiley & Sons, N.Y., 3d ed. 1979) and evaporation is discussed in F. Standiford, "Evaporation", *Encyclopedia of Chemical Technology*, vol. 9, pp. 472–493 (Kirk-Othmer, eds. John Wiley & Sons, N.Y., 3d ed. 1980), the disclosures of which are incorporated by reference.

Distillation of the alkyl fatty acid esters can be accomplished as described in U.S. Pat. No. 5,190,618 (Top et al.), the disclosure of which is incorporated by reference. In that patent, distillation equipment consists of a high heat-transfer distillation column, i.e. a high heat-transfer rate falling film distillation column, and distillate collection system. The distillation process is continuous. Alkyl esters are distilled at high vacuum at below about 10 mm of Hg (1333 N/m$^3$) and at a temperature between about 100° C. and about 200° C. Distilled alkyl esters are collected by condensation and discharged as a by-product. The retention time of the tocopherols and sterols in the distillation column is short, so that deterioration is minimal. More than one distillation cycle may be practiced, but is clearly undesirable because of degradation of the bottoms, particularly the tocopherols (which tend to be particularly susceptible to heat-induced degradation).

Distillation of alkyl fatty esters is, however, preferably conducted as disclosed in PCT publication WO 95/04731, published Feb. 16, 1995, the disclosure of which is incorporated herein by reference. That distillation employs a packed distillation column at a moderate temperature (i.e. lower than the reboiler evaporator temperature) and an evaporator at a higher temperature (i.e. higher than the temperature to which the packed column is heated) in which the liquid phase will have minimal residence time, such as in a wiped-film evaporator. This distillation is preferably accomplished by introducing a pre-heated liquid into essentially the mid-point of a packed column, removing the bottoms of the packed column to a wiped film evaporator, and removing the bottoms from the wiped film evaporator to a zone of ambient temperature. The vapor phase from the wiped film evaporator re-enters the packed column through the bottom of the column. The packed column will typically be configured to provide about 5–12 theoretical stages or plates above the point of introduction and about 5–12 theoretical stages or plates below the point of introduction and will typically be operated with a temperature and pressure at the top of the column of about 120° C. to about 150° C. and about 0.1 mbar to about 3 mbar and at the bottom of the column at about 180° C. to about 220° C. and about 3 mbar to about 9 mbar, with a reflux ratio of about 0.4 to about 0.6 and distillate as a percentage of feed (based on weight) of about 60% to about 80%. This column is thus operated at a temperature that is lower than the temperature employed in the wiped film evaporator reboiler.

The wiped film evaporator will typically be operated as a reboiler for the packed column with a temperature of about 200° C. to about 300° C., typically at about 260° C. and pressure of about 3 to about 12 mbar. The mechanical agitation of the film within the wiped film evaporator will ensure that the mixture of tocopherols and sterols will have a short residence time at the high temperatures employed. This will minimize degradation of the tocopherols and sterols and thus enhance the overall yields. The mechanical agitation of the film will preferably ensure that contact of any particular portion of the mixture of tocopherols and sterols with the heat exchanger surface is essentially instantaneous with removal thereof from such contact (e.g. by bringing such portion to the surface of the film in contact with the reduced pressure atmosphere maintained within the evaporator where evaporative cooling will lower the temperature of that portion of the mixture). Of course, such portion of the film can again come in contact with the surface of the heat exchanger, but will again be removed from contact therewith by the mechanical agitation. Further, the mechanical agitation will act to shorten the overall residence time in the evaporator of any particular portion of the mixture.

The distillation sequence described above will typically effect an essentially complete separation of alkyl fatty acid esters from the admixture with tocopherols and sterols. For example, the ultimate bottoms will contain less than about 1%, typically less than about 0.5%, of alkyl fatty acid esters. However, it may be desirable under certain circumstances to perform only a partial removal of alkyl fatty esters from such a mixture. Such a partial removal is advantageously accomplished by the process described above, but dispensing with the use of the packed column, i.e. by the use of a falling film evaporator or a wiped film evaporator.

The partial stripping will be particularly advantageous if used to remove a portion of the alkyl fatty esters from a mixture wherein the weight ratio of alkyl fatty esters to total weight of tocopherols and sterols combined ranges from about 1.5:1 to about 5:1. The stripping will typically be effective in removing from about 30% to about 60% of said mixture (i.e. the esterified feed) as alkyl fatty esters while removing only nominal amounts of tocopherols and sterols, e.g. the alkyl fatty esters will contain less than about 5% by weight, typically less than about 3% by weight, of tocopherols and sterols combined.

The product of the distillation step will be enriched in tocopherols and sterols. The tocopherols and sterols can be separated from the mixture by any of a variety of means, e.g. chromatographic separation based on differential solubility and/or adsorption or other interaction with a solid phase. Preferred, however, is a method in which the mixture is dispersed in a particular solvent system which facilitates the formation of a liquid phase enriched with respect to the mixture in tocopherol compounds and a solid phase enriched with respect to the mixture in sterol compounds and then physical separation of the liquid and solid phases. This can be considered a crystallization process. Crystallization processes are discussed in the *Encyclopedia of Chemical Technology*, vol. 7, pp. 243–285 (Kirk-Othmer, eds. John Wiley & Sons, N.Y., 3d ed. 1979), the disclosure of which is incorporated herein by reference.

The preferred method of separating one or more tocopherol compounds from one or more sterol compounds of the mixture is described in PCT publication WO 95/04731, published Feb. 16, 1995, the disclosure of which is incorporated herein by reference. The process described therein typically begins with dispersing a mixture of one or more tocopherol compounds and one or more sterol compounds, said mixture being essentially free of higher fatty acid compounds, in a solvent mixture comprised of a major amount of a low polarity organic solvent, a minor amount of a high polarity organic solvent, and a minor amount of water.

In the broadest sense, the high polarity solvent will be an organic solvent having a higher polarity (as measured for example by the dielectric constant of a pure liquid phase of the solvent at under ambient conditions, e.g. room temperature) than the low polarity organic solvent, and vice versa. The low polarity organic solvent will preferably have a dielectric constant of less than about 25, more preferably less than about 1 0, and the high polarity solvent will preferably have a dielectric constant of more than about 25, more preferably more than about 30. The dielectric constants of various organic solvents are set forth in the *Handbook of Chemistry and Physics*, pp. E-56 to E-58 (CRC Press, Inc., Cleveland, Ohio, 55th ed., 1974), the disclosure of which is incorporated herein by reference. Typically, the low polarity organic solvent will be a hydrocarbon solvent, i.e. one consisting solely of carbon and hydrogen atoms, or an oxygenated hydrocarbon solvent, e.g. one consisting solely of carbon, hydrogen, and oxygen and having less than one oxygen atom per carbon atom.

Preferred low polarity organic solvents are the higher alkanes (of sufficiently high molecular weight to form a liquid phase that can be practically handled, preferably straight-chain or branched-chain alkanes having from 6 to 12 carbon atoms), e.g. hexane, heptane, n-octane, iso-octane, 2,2,4-trimethylpentane, nonane, or decane; monoketones, e.g. acetone, 2-butanone, or 2-octanone; monoaldehydes, e.g. acetaldehyde or propionaldehyde; monoesters, e.g. ethyl formate or ethyl acetate; higher monohydric alcohols, e.g. n-propanol, iso-propanol, n-butanol, sec-butanol, n-hexanol, or 2-ethylhexanol. Preferred high polarity organic solvents are low molecular weight, oxygenated hydrocarbons, preferably the lower alkanols such as methanol or ethanol. The solvent blend will also preferably comprise a minor amount of water.

The solvent blend will be comprised of a major amount of the low polarity organic solvent, i.e. greater than about 50% by weight of the solvent blend, typically at least about 80% and preferably from about 90% to about 99.5%, e.g. from about 92.0% to about 99.0%. The high polarity organic solvent will be present in a minor amount, i.e. less than about 50% by weight of the solvent blend, typically less than about 20% and preferably from about 0.5% to about 10%, e.g. from about 1.0% to about 8.0%. Water is preferably present in an amount essentially equal to the high polarity organic solvent, e.g. in a ratio of high polarity organic solvent to water of from about 5:1 to about 1:5, more typically from about 3:1 to about 1:3. Thus, preferred solvent blends are comprised of from about 80% to about 99% by weight of a member selected from the group consisting of higher alkanes, from about 0.5% to about 20% of methanol or ethanol, and from about 0.5% to about 5% by weight of water.

The solvent blend and mixture of tocopherols and sterols are mixed to form what is initially a substantially homogeneous liquid phase. The mixture can be heated, e.g. to the atmospheric boiling point of the solvent blend, to obtain a homogeneous liquid mixture. The ratio of solvent blend to feed mixture may vary, but will typically be from about 10:1 to about 1:1, preferably from about 5:1 to about 3:1. The resulting mixture is maintained under conditions, typically at a reduced temperature, to produce a liquid phase enriched in tocopherol compounds and a solid phase enriched in sterol compounds. The temperature of the mixture should be maintained below ambient, e.g. less than about 25° C., typically from about −40° C. to about 20° C., more typically from about −25° C. to about 0° C. The mixture can be cooled from the temperature of its dispersion to a reduced temperature at a variety of cooling rates, e.g. at relatively fast rates of about 80° C. per hour to about 120° C. per hour or relatively slow rates of about 2.5° C. to about 10° C. per hour.

The sterols crystallize or otherwise precipitate to form a solid phase that can be physically separated from the liquid phase, e.g. by filtering, centrifuging, or decanting. Preferably, the solid phase collected will be at least about 90% (typically at least about 92%) by weight sterols with less than about 5% (typically less than about 2%) tocopherols and the liquid phase (mother liquor) will have a ratio of tocopherols to sterols of greater than abut 5:1 (typically greater than about 10:1). The mother liquor is enriched in tocopherols (with respect to the feed to the crystallization) and can be further purified by distillation to collect more highly purified tocopherols as distillate.

All parts, percentages and ratios in this specification and the appended claims are by weight, unless otherwise specified. The following examples are intended to illustrate the invention without limiting it in any way.

EXAMPLES

Example 1

A vegetable oil deodorizer product containing free fatty acids and fatty glycerides along with about 10% by weight tocopherols, about 4% free sterols, about 13% by weight total sterols (total of free sterols and sterol esters) and an acid value of about 76 is mixed with an amount of dry methanol equal to about 50% by weight of the product and an amount of zinc oxide equal to about 0.1% by weight of the product. This mixture is heated in a pressurized vessel to a temperature of about 200° C. and held for about 2 hours. The product is then allowed to cool below the boiling point of the methanol and the methanol is distilled by simple distillation. The distillate bottoms are then washed with aqueous sulfuric acid (about 5% by weight sulfuric acid in water) and then washed with water until the pH of the organic phase is from about 6 to about 8. The product is then dried.

Example 2

The product of Example 1 is mixed with an amount of dry methanol equal to about 50% by weight of the product and an amount of sodium methoxide equal to about 0.2% by weight of the product. This mixture is heated in a pressurized vessel to a temperature of about 200° C. and held for about 2 hours. The product is then allowed to cool below the boiling point of the methanol and the methanol is distilled by simple distillation. The distillate bottoms are then washed with aqueous sulfuric acid (about 5% by weight sulfuric acid in water) and then washed with water until the pH of the organic phase is from about 6 to about 8. The product is then dried.

What is claimed is:

1. A process useful in the recovery of tocopherols from a tocopherol mixture comprised of fatty acids and tocopherols, said process comprising esterifying free fatty acids present in said tocopherol mixture and transesterifying fatty acid glyceride esters present in said tocopherol mixture by mixing said tocopherol mixture with a lower alcohol in the presence of a zinc catalyst selected from the group consisting of zinc oxide, zinc hydroxide, and mixtures thereof, to form a reaction mixture in a reaction vessel, the temperature of said reaction mixture being above the atmospheric boiling point of said alcohol and the pressure within said reaction vessel being sufficient to maintain at least a major proportion of said alcohol in a liquid phase.

2. The process of claim 1 wherein said lower alcohol is a member selected from the group consisting of primary and secondary mono-alkanols having less than five carbon atoms.

3. The process of claim 1 wherein the product of the process is dried and mixed with a lower alcohol in the presence of an alkoxide catalyst selected from the group consisting of alkali metal alkoxides of said alcohol, to form a reaction mixture in a reaction vessel, the temperature of said reaction mixture being above the atmospheric boiling point of said alcohol and the pressure within said reaction vessel being sufficient to maintain at least a major proportion of said alcohol in a liquid phase.

4. The process of claim 3 wherein the process further comprises distilling excess lower alcohol from the product of said process.

5. The process of claim 4 wherein said process further comprises washing the product of said process to remove glycerol produced by said transesterification.

6. The process of claim 5 wherein said washing comprises a first washing with an aqueous mineral acid followed by a washing with pure water.

7. The process of claim 1 wherein said lower alcohol is a $C_1$ to $C_4$ mono-hydric alkanol.

8. The process of claim 1 wherein said lower alcohol is selected from the group consisting of methanol, ethanol, n-propanol, isopropanol, n-butanol, and tert-butanol.

9. The process of claim 1 wherein the amount of said lower alcohol is equal in mass to from about 20% to about 80% with respect to the mass of original tocopherol containing starting material.

10. The process of claim I wherein the amount of said lower alcohol is equal in mass to from about 50% to about 60% with respect to the mass of original tocopherol containing starting material.

11. The process of claim 1 wherein the amount of said zinc catalyst is from about 0.005% to about 5% by weight of the tocopherol mixture.

12. The process of claim 1 wherein the amount of said zinc catalyst is from about 0.01% to about 1% by weight of the tocopherol mixture.

13. The process of claim 1 wherein the amount of said zinc catalyst is from about 0.05% to about 0.2% by weight of the tocopherol mixture.

14. The process of claim 1 wherein said esterifying and transesterifying are conducted at a temperature between about 150° C. and about 240° C.

15. The process of claim 1 wherein said esterifying and transesterifying are conducted over a time of about 1 to about 3 hours.

16. The process of claim 1 wherein a major proportion of the fatty acids and fatty glyceride esters are esterified to produce alkyl fatty esters.

17. The process of claim 1 wherein more than about 50% by weight of the fatty acids and fatty glyceride esters are esterified to produce alkyl fatty esters.

18. The process of claim 1 wherein at least about 90% by weight of the fatty acids and fatty glyceride esters are esterified to produce alkyl fatty esters.

19. The process of claim 1 wherein the product is further transesterified in the presence of an alkoxide catalyst to effect essentially complete conversion of sterol esters to free sterols.

20. The process of claim 19 wherein the alkoxide catalyst is a lower alkoxide.

21. The process of claim 20 wherein said catalyst is sodium methoxide in methanol.

22. A process useful in the recovery of tocopherols from a tocopherol mixture comprised of fatty acids and tocopherols, said process comprising esterifying free fatty acids present in said tocopherol mixture and transesterifying fatty acid glyceride esters present in said tocopherol mixture by mixing said tocopherol mixture with methanol in an amount of from about 20% to about 80% by weight of said tocopherol mixture, in the presence of a zinc catalyst selected from the group consisting of zinc oxide, zinc hydroxide, and mixtures thereof, in an amount of from about 0.005% to about 5% by weight of the tocopherol mixture, to form a reaction mixture in a reaction vessel, the temperature of said reaction mixture being above the atmospheric boiling point of methanol and the pressure within said reaction vessel being sufficient to maintain at least a major proportion of said alcohol in a liquid phase.

\* \* \* \* \*